US009279099B2

(12) United States Patent
Okano et al.

(10) Patent No.: US 9,279,099 B2
(45) Date of Patent: Mar. 8, 2016

(54) PROCESSING SYSTEM FOR CELL CULTURES AND MODULE CONNECTING METHOD OF PROCESSING SYSTEM FOR CELL CULTURES

(71) Applicant: Tokyo Women's Medical University, Shinjuku-ku (JP)

(72) Inventors: Teruo Okano, Shinjuku-ku (JP); Tatsuya Shimizu, Shinjuku-ku (JP); Masanori Wada, Shinjuku-ku (JP); Yukito Yamasaki, Tsukuba (JP)

(73) Assignee: TOKYO WOMEN'S MEDICAL UNIVERSITY, Shinjuku-ku (JP)

( * ) Notice: Subject to any disclaimer, the term of this patent is extended or adjusted under 35 U.S.C. 154(b) by 0 days.

(21) Appl. No.: 13/745,247

(22) Filed: Jan. 18, 2013

(65) Prior Publication Data
US 2013/0130361 A1     May 23, 2013

Related U.S. Application Data

(63) Continuation of application No. PCT/JP2012/050064, filed on Jan. 5, 2012.

(30) Foreign Application Priority Data

Jan. 17, 2011    (JP) .................................. 2011-007351

(51) Int. Cl.
*C12M 1/38*    (2006.01)
*C12M 3/00*    (2006.01)
(Continued)

(52) U.S. Cl.
CPC ............... *C12M 23/44* (2013.01); *C12M 23/50* (2013.01); *C12M 37/00* (2013.01); *C12M 41/48* (2013.01); *F16L 55/00* (2013.01); *Y10T 137/0402* (2015.04)

(58) Field of Classification Search
CPC ...... C12M 23/34; C12M 23/44; C12M 37/00; C12M 37/04; C12M 41/14; A61L 2/18; A61L 2/206; A61L 2/208; B01L 1/02; B01L 1/025
USPC .................................... 435/303.1, 287.3, 809
See application file for complete search history.

(56) References Cited

U.S. PATENT DOCUMENTS 3,907,389 A * 9/1975 Cox et al. .......................... 312/1
5,892,200 A * 4/1999 Kendall et al. ................ 219/201
(Continued)

FOREIGN PATENT DOCUMENTS

CN      1453352 A      11/2003
JP      2004-350640 A  12/2004
(Continued)

OTHER PUBLICATIONS

International Search Report issued Mar. 19, 2012 in PCT/JP2012/050064 filed Jan. 5, 2012.
(Continued)

*Primary Examiner* — William H Beisner
(74) *Attorney, Agent, or Firm* — Oblon, McClelland, Maier & Neustadt, L.L.P.

(57) ABSTRACT

A processing system for cell cultures for carrying out cell/tissue culturing processes in the field of regenerative medicine, etc. which is a processing system for cell cultures which prevents viruses and human-derived cells, etc. other than a culturing processing target from entering the interior of a closed space from outside of the system to maintain sterility, maintains sealability of the closed spaces of modules, and couples or detaches the plurality of modules in accordance with a wide variety of cell culturing processing steps so that cell culturing processes can be carried out by combining the plurality of culturing processing modules is provided.

10 Claims, 11 Drawing Sheets

(51) Int. Cl.
*F16L 55/00* (2006.01)
*C12M 1/00* (2006.01)
*C12M 1/12* (2006.01)
*C12M 1/36* (2006.01)

(56) References Cited

U.S. PATENT DOCUMENTS

2004/0215362 A1* 10/2004 Kokubo et al. ............... 700/130
2006/0151185 A1   7/2006 Takagi et al.
2006/0275888 A1  12/2006 Hibino et al.
2012/0077220 A1   3/2012 Mizutani et al.

FOREIGN PATENT DOCUMENTS

| JP | 2005-253331 | 9/2005 |
| JP | 2006-115798 A | 5/2006 |
| JP | 2008-54690 A | 3/2008 |
| JP | 2011-004613 A | 1/2011 |

OTHER PUBLICATIONS

Biosafety Laboratory Construction, "7.6 Transmission Window," Chemical Industry Press, p. 246, Apr. 30, 2006 (w/ English Translation).

* cited by examiner

PROCESSING SYSTEM FOR CELL CULTURES AND MODULE CONNECTING METHOD OF PROCESSING SYSTEM FOR CELL CULTURES

CROSS REFERENCE TO RELATED APPLICATIONS

This application claims priority to PCT/JP2012/50064 filed on Jan. 5, 2012, the entire contents of which are incorporated by reference herein.

TECHNICAL FIELD

The present invention relates to a processing system for cell cultures in the field of medicine, biology, drug development, pharmacy, etc. The present invention particularly relates to a processing system of cells, tissues, organs, etc. (hereinafter, referred to as cells) for regenerative medicine or biomedical production.

BACKGROUND ART

Recently, expectations for regenerative medicine that repairs lost or function-deteriorated cells by using human or animal cells have been increasing. Also, research of proliferation and tissue engineering of somatic cells and somatic stem cells have been developing. Furthermore, research of ES cells and development of the techniques to create and proliferate iPS cells have been developing. In order to culture and organize the cells in vitro used for such medical treatment, a processing system for cell cultures which has improved safety, quality, high-throughput achievement and manufacturing cost, has been desired.

However, in order to carry out medical treatment by transplantation of cells into a human or animal body, proliferation, differentiation or organization of cells has to be carried out effectively and efficiently. In addition, ensuring safety is important. Two conditions are required to ensure safety as mentioned above. First, in the environment in which the cells are processed, it is necessity to prevent foreign matters, dust and germs from entering the environment, and keep the environment sterility. Secondly, particularly in the case of culturing the cells derived from a patient (autologous cell culture), it has to be prevented to contaminate the patient's cells with other people's cells, non-human cells, viruses, bacteria, etc. Moreover, it has to be eliminated the bacteria and non-target cells from target cells.

Conventionally, in order to ensure safety, culturing cells have been carried out in a large clean room, which maintains the entire room clean atmosphere. This clean room is a very expensive facility since an equipment cost and a maintenance cost are extremely high. Therefore, the cost of cultured cells is also significantly increased.

Culturing process and procedure by using an automated cell-culturing system need to be recorded and saved as well as by culturing cells manually. In the automated cell-culturing system, it is desired to carry out recording and saving culturing process and procedure more efficiently and precisely than the case in which they are carried out by culturing cells manually.

A step of culturing cells includes various steps. The steps are not particularly limited, and examples of the steps include: a step of separating cells from a tissue obtained from a human or non-human, a step of isolating target cells from the separated cells, a step of primary-culturing cells, a step of expansion of cells, a step of sub-culturing, a step of differentiating cells to arbitrary (desired) cells, a step of organizing cells, and a step of packaging cells/tissues. These steps may be appropriately selected in accordance with, for example, the purpose of medical treatment and cell type and are not particularly limited. When a myoblast sheet utilized for heart failure is to be prepared, the cell sheet is prepared through: a step of obtaining muscle tissues from a patient and isolating and primary-culturing myoblasts, a step of expansion of myoblasts, a step of sub-culturing myoblasts, and a step of preparing monolayered myoblast sheets, and a step of stacking monolayerd myoblast sheets. When a cell sheet is to be prepared for heart failure by utilizing ES cells or iPS cells, the cell sheet is prepared through: a step of expansion of ES cells or iPS cells, a step of differentiating ES cells or iPS cells into arbitrary cells such as myoblasts or cardiomyocytes, a step of preparing monolayered cell sheets, and a step of stacking them. When a cell sheet for corneas disease is to be prepared, the sheet is prepared through: a step of obtaining oral mucosa tissues, a step of isolating cells from the tissues, and a step of preparing monolayer-cell sheets. In those steps of culturing cells, the steps described above and other steps can be combined depend on the purpose of culture. Therefore, in culturing of cells, there are several cases, such as carrying out a part of the steps described above selectively, carrying out the steps in changing order of the steps, and repeating a part or all of the steps. Moreover, the time required for carrying out the steps is different depending on each step.

PRIOR ART DOCUMENT

Patent Document

Patent Document 1: Japanese Patent Application laid-open No. 2008-054690
Patent Document 2: Japanese Patent Application laid-open No. 2004-350640
Patent Document 3: Japanese Patent Application laid-open No. 2011-4613

SUMMARY OF THE INVENTION

Problems to be Solved by the Invention

A conventional processing system for cell cultures is large and complex so that various cell culturing processes can be carried out. Therefore, the conventional system has a problem that cost of the system is extremely high.

The present invention has been accomplished in view of these problems. A processing system for cell cultures of the present invention provides a system capable of culturing and processing a wide variety of cells at low cost. It also provides a rational processing system for cell cultures capable of flexibly processing and culturing various cells/tissues, etc. in accordance of the purpose.

Means for Solving the Problems

A processing system for cell cultures of the present invention is characterized by comprising, a plurality of modules that can be mutually connected; a first closed space provided in each of the modules; a door that opens/closes an aperture possessed by the first closed space; a connecting member provided at a peripheral part of the aperture; and a decontaminating-agent supplying module that supplies a decontaminating agent; wherein the decontaminating agent is supplied to the first closed space by the decontaminating-agent supplying module; the decontaminating agent is supplied to a second closed space formed by the connecting member and the door of one module and the connecting member and the door of the other module connected to the one so as to form an integrated closed space, maintaining the connected modules in a sterile state.

The processing system for cell cultures of the present invention can increase/decrease the number of module(s) (unit(s)) easily (detaching module(s) from the system and connecting module(s) to the system) depending on the culturing process, throughput, and production volume.

The processing system for cell cultures of the present invention can carry out various cell culturing processes in the first closed space. In the processes, the doors are closed for maintaining environmental conditions (temperature, humidity, sterility, etc.) to carry out the cell culturing processes. As a result, the first closed space is isolated from the external atmosphere (outside of the closed space). When compared with a conventional semiconductor manufacturing system provided with a closed space, it is common in the point that a door (gate valve) is closed and the interior space of chamber is closed in order to maintain the interior of chamber with predetermined temperature or vacuum so that wafers can be manufactured.

However, the processing system for cell cultures of the present invention is different from the conventional system in the below points. The processing system for cell cultures of the present invention can physically separate module(s) from a system and move the position thereof. The detached module can maintain the environment in the first closed space by closing the door thereof. In the processing system for cell cultures of the present invention, after the interior of the first closed space is decontaminated/sterilized and decontaminating/sterilizing operation is stopped, the sterilized state of the interior of the first closed space can be maintained for a certain period with the door which can seal/open the first closed space.

As a module-attachable/detachable conventional system which is provided with a plurality of modules, there is a system in which a door (or cover) of a module to be connected with the other and a door (or cover) of the other module are connected with each other, and both of the doors (or covers) are opened at the same time so that the closed spaces of both of them can be communicatably connected. However, in such a conventional cell culturing system, the outside of the doors (outside of the first closed spaces) is brought into contact with outside air, and cells derived from another human different from the human-derived cells serving as a target of a cell culturing process, various germs, etc. may be attached thereto. Therefore, when the modules are to be connected again, the human-derived cells which are not the culturing processing target, various germs, etc. are brought into the closed space while they are attached to the outside of the doors, and they may contaminate the cells serving as the cell processing target. Therefore, in order to prevent contamination of the outside of the doors of the modules of the conventional cell culturing system, the system has been required to be installed in a clean room of an atmosphere having a high clean degree (not during operation: class 10,000 or less, during operation: class 100,000 or less). Furthermore, workers have been required to pay keen attention to clothing (clothing such as so-called clean wear, mask, and gloves) and operation methods so that the outside of the doors of the modules are not contaminated by the workers.

On the other hand, in the processing system for cell cultures of the present invention, between the first closed space of a module to be connected with the other and the first closed space of the other module, the second closed space is sealably formed by the doors of both of the modules and the connecting members of both of the modules, and the modules are connected after decontamination/sterilization is carried out by supplying the decontaminating agent into the closed space. As a result, in the system of the present invention, all the part which has been in contact with the outside atmosphere before connection is decontaminated, and the integrated decontaminated/sterilized safety sterile space is formed without bringing germs, etc. into the closed space; therefore, cell culturing processes can be carried out under an optimum environment. When the first closed space and the second closed space are decontaminated/sterilized in this manner, a cell culturing system can be installed even in a clean room of an atmosphere having a clean degree (not during operation: class 100,000 or less) lower than the conventional cases. Even if a worker contaminates the outside of the door of the module, preventive measures of contamination carried out by the worker can be reduced since the modules are connected with each other after the outside of the doors of the modules are decontaminated/sterilized in the system of the present invention.

According to another aspect of the processing system for cell cultures of the present invention, the system is provided with module control devices and an integrated control device. The module control device controls the module so that the module executes a predetermined process in accordance with a command. The integrated control device is electrically connected with the module control devices of the modules connected via the connecting members each other and thus the integrated control device controls the operation of each module. This processing system for cell cultures is characterized by carrying out, by the integrated control device, communication with the plurality of connected modules, recognizing IDs of the modules, and carrying out operation commands in accordance with the IDs with respect to the modules so as to associate the plurality of connected modules to process a series of processing steps of various culturing processes comprehensively or separately execute the various cell culturing processes.

In the steps of carrying out the cell culturing processes, the cell processing time and the amount of the cells obtained as a result of the cell culturing processes are different depending on the cell type or individual differences in the case of human-derived cells. Even in such a case, in the processing system for cell cultures of the present invention, modules can be separately and additionally connected during the cell culturing processes; specifically, the modules can be detached, and the modules can be separately connected and added. Moreover, according to the processing system for cell cultures of the present invention, while a cell culturing process is carried out, another cell culturing process can be carried out. In this case, the module which has been used in a previous cell culturing processing step and become unnecessary in the next step can be detached, and a module which is required for a next cell culturing processing step can be coupled. Thus, the system can support many types of culturing processes of cells or tissues at the same time by changing module in such a manner. Moreover, coupling or detachment of the plurality of modules can be recognized by providing distinguishable unique IDs for the modules and reading the IDs respectively. Furthermore, the measurement result of the operation logs, communication logs, and environmental information of the modules can be configured to be transmitted to the integrated control device as electric signal (s) together with the IDs of the modules as the information source thereof, and recorded in the storage unit. Thus, the cells. serving as specimens can be accurately managed so that they are not mixed with other cells.

According to another aspect of the processing system for cell cultures of the present invention, the system further comprises a conveyance module provided with a conveyance robot inside, and each modules are connected to the conveyance module. The conveyance robot is characterized by moving a conveyance object from the first closed space of one of the connected modules to the first closed space of the other module via the second closed space.

Since the conveyance module is provided, the processing system for cell cultures can convey plates and bottles, which contain cells, media, and so on, and other materials required for cell culturing processing operations, and thus they are conveyed in the closed spaces in the processing system for cell cultures or in a space between other closed spaces. As a result, the plurality of sterile closed spaces possessed by the processing system for cell cultures can be integrally used to carry out various cell culturing processes.

According to another aspect of the processing system for cell cultures of the present invention, the connecting member is provided with a sealing member of which interior has a hollow shape and an injecting means which injects a gas, etc. into the sealing member. The sealing member can be swelled by injecting a gas, liquid, or gel-like matter into the interior of the sealing member. As a result, the gap between a connecting member and the other connecting member can be filled, and the interior of the second closed space can be hermetically sealed.

In this processing system for cell cultures, the sealing member filling the gap between the connecting members can prevent the decontaminating agent from leaking from the gap between the connecting members to the outside and from contaminating with germs and other cells from outside during execution of the cell culturing process.

Moreover, in the processing system for cell cultures, even if a slight gap is caused between the connecting members at the time of connecting the plurality of module, the gap can be filled with the sealing member. A gas, etc. (gas, etc. refer to gas, liquid, gel-like matter, etc.) is injected into the sealing member to swell the sealing member and bring the sealing member and the connecting member or the sealing member and another sealing member into close contact with each other so that the gap between the connecting members can be filled. As a result, the interior of the second closed space can be reliably shut off from outside air.

A module connecting method of the processing system for cell cultures of the present invention is characterized by including: a step of connecting the plurality of modules via the connecting member; a step of supplying the decontaminating agent to the second closed space formed by the plurality of connecting members and the plurality of doors from the decontaminating-agent supplying module to decontaminate interior of the second closed space; and a step of opening the doors to communicate the first closed space and the second closed space with each other so as to form an integrated sterile closed space.

According to the module connecting method of the processing system for cell cultures, the sealing member (seal receiving member for the opposed side) is provided on both of or one of the connecting members of one and the other modules. As a result, the doors can be opened to mutually communicate a plurality of closed spaces after the region formed by the doors and the connecting members is decontaminated to carry out decontamination/sterilization. Therefore, contamination with germs, foreign matters and other cells which adversely affect the cell culturing process in the closed space can be prevented. Moreover, the processing system for cell cultures of the present invention can change modules by separating the module, which has become unnecessary during a processing step while the cell culturing process is carried out, and connecting another module.

According to another aspect of a module connecting method of the processing system for cell cultures of the present invention, the method is characterized by including: a step of installing the plurality of modules with a gap therebetween; a step of swelling sealing members provided on the plurality of modules so as to fill the gap and connect the plurality of modules; a step of supplying the decontaminating agent to the second closed space formed by the plurality of connecting members and the plurality of doors from the decontaminating-agent supplying module to decontaminate interior of the second closed space; and a step of opening the doors to communicate the first closed space and the second closed space with each other and form an integrated sterile closed space.

According to the module connecting method of the processing system for cell cultures of the present invention, after the plurality of modules are moved to connecting positions (at this time, the positions providing a gap between the connecting members and the sealing members of both of the modules), a gas, etc. (gas, etc. refer to gas, liquid, gel-like matter, etc.) is injected into the interior of the hollow-shaped sealing member so as to swell the sealing member and to fill (seal) the gap between the connecting members. As the result, the interior of the second closed space can be shut off from outside air.

Therefore, breakage accidents, deterioration due to wearing, generation of dust caused by collision and contact directly between the seal members due to the module connection can be reduced, and leakage of the gas, etc. from the inside/outside of the second closed space can be prevented for a long period of time.

Effects of the Invention

The processing system for cell cultures of the present invention can increase/decrease the number of the processing modules used in the system while carrying out reliable decontamination/sterilization. As a result, there are advantages that the degree of freedom of the combination of the processing modules can be significantly improved and that many types of culturing processes of cell, tissues, etc. can be supported.

BRIEF DESCRIPTION OF THE DRAWINGS

FIGS. 5A and 5B show perspective views showing a door 25a.

BEST MODES FOR CARRYING OUT THE INVENTION

A processing system for cell cultures composed of various modules used in many types of culturing processes is realized with a minimum floor occupying area and reduced processing time.

Figure 1:
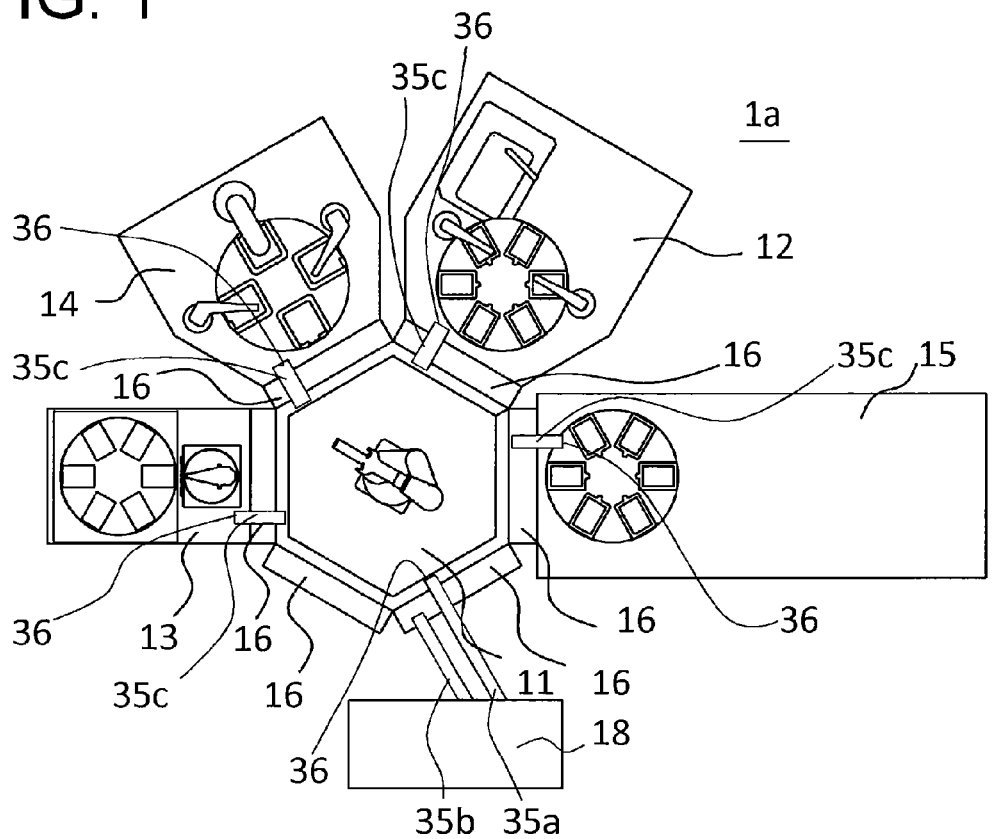
FIG. 1 is a plan view showing a processing system for cell cultures.

FIG. 1 is a plan view of an embodiment of a processing system for cell cultures of the present invention. Reference numeral 1a of FIG. 1 denotes the embodiment of the processing system for cell cultures, 11 denotes a conveyance module, 12 denotes a dispensing module, 13 denotes a homothermal module, 14 denotes a cell-sheet stacking module, and 15 denotes a carry-out/in module of, for example, a culturing plate. These modules 11 to 15 are shown as examples and may be modules having other functions. More modules may be connected thereto.

Attaching/detaching means 16 are provided at lateral surfaces of the hexagonal conveyance module 11 at the center of the drawing. The attaching/detaching means 16 detachably connect the conveyance module 11 with the modules represented by 12 to 15. The conveyance module 11 and the other modules 12 to 15 (also referred to as processing devices) are provided with closed spaces (for example, chamber or housing) which shut off outside air. After the conveyance module and the other modules are mutually connected, one closed space or sealed space can be formed as a whole system, alternatively, a closed space or a sealed space, which is completely sealed, separated by an openable/closable door can be formed in each module unit.

In the present embodiment, when the conveyance module and the other modules are mutually connected, decontaminating/sterilizing-gas supplying pipes 35a to c (decontaminating/sterilizing-gas supplying apertures 36) from a decontaminating-agent supplying module 18 are also connected. As a result, a decontaminating agent can be supplied into the processing modules, and every part in a cell stacking system 1a can be decontaminated/sterilized. Note that 35a represents a sterilizing-gas supplying pipe for directly supplying the decontaminating agent from the decontaminating-agent supplying module 18 to the conveyance module 11, and the pipe 35b is a module 18-side sterilizing-gas supplying pipe, which supplies the decontaminating agent from the decontaminating-agent supplying module 18 to the other modules 12 to 15. Each of the pipes 35c is coupled to the pipe 35b via a pipe (not shown) in the conveyance module 11. The pipes 35c are module 12 to 15-side sterilizing-gas supplying pipes, which supply the decontaminating agent from the decontaminating-agent supplying module 18 to the other modules 12 to 15. The decontaminating-agent supplying pipes 35 are not limited to be piped to the other modules via the conveyance module like the present embodiment. As another embodiment, the pipes may be configured to be directly piped from the decontaminating-agent supplying module.

The processing system for cell cultures 1a as described may be provided with a closed space such as a chamber in each module and have a clean atmosphere (1000 class or less, desirably, 100 class or less), wherein a fan filter module is provided on the chamber. The fan filter module is composed of, for example, a fan, which blows clean air into the chamber, and a filter, which prevents dust, viruses, etc. contained in the blown air from being carried into the chamber. The fan and the filter are provided to be close to each other as an integrated module. Alternatively, they may be provided so as to be at the positions away from each other by interposing a ventilation pipe between the fan and the filter.

The processing system for cell cultures 1a can connect modules via the attaching/detaching means 16; therefore, the number of modules can be increased/decreased. Therefore, there is an advantage that the combinations of the modules can be changed depending on culturing processes of many types of cells, tissues, etc. For example, the uses include: carrying cell suspensions into, cell seeding onto culturing plates, medium replacement, stacking of cell sheets, carrying stacked cell tissues out.

For example, the decontaminating-agent supplying module 18 shown in the present embodiment is provided with: a liquid supplying means which supplies hydrogen peroxide liquid; a vaporizing (gasifying) means which vaporizes the hydrogen peroxide liquid; a gas supplying means which supplies a gas to the modules; gas pipes which connect the parts between the modules and the gas supplying means; pipes which collect discharged gases from the modules; and a gas discharging pipe which detoxifies the collected gases through a catalyst and discharges the gases.

A hydrogen peroxide gas generated by the decontaminating-agent supplying module 18 can be flown into a first closed space and a second closed space (described later) of each of the modules. Thus, bacteria, human-derived cells in the first closed space 23 (including an actuator, sensor, container exterior, etc. provided in the module such as conveyance module) can be killed. The type of the decontaminating agent supplied from the decontaminating-agent supplying module 18 is not particularly limited. For example, the decontaminating agent may be hydrogen peroxide like the present embodiment or may be acetyl hydroperoxide, formaldehyde, ozone and/or chlorine dioxide. Particularly, it is preferred to supply these as a decontaminating agent made into vapor, gas, or mist.

By using the processing system for cell cultures of the present invention, cells derived from one or plural patients may be subjected to cell culturing and processing operations simultaneously and parallelly. Even in the case of the cells derived from a single patient, the cells of plural types having different culturing steps may be handled simultaneously and parallelly. An embodiment of a case in which cells derived from plural patients are subjected to cell culturing and processing operations simultaneously and parallelly by using the processing system for cell cultures of the present invention will be explained below.

By using the processing system for cell cultures 1a of the present invention shown in FIG. 1, a cell culturing process is carried out for cells derived from a certain human. While cell culturing is carried out in the homothermal module, the decontaminating agent is injected into the first closed spaces (later-described V1 region) of the dispensing module, the conveyance module, and the carry-out/in module used in a previous step and the second closed spaces (later-described V2 region) connecting those modules to carry out decontamination/sterilization. Then, cells derived from another human are brought into the processing system for cell cultures by using the carry-out/in module, and a cell culturing process as same as the process done for the previous human's cell or another cell culturing process is carried out.

Therefore, in the cell culturing system of the present invention, cell culturing processes of different types or a single type can be carried out simultaneously for the cells derived from plural humans or derived from a single human. Furthermore, regarding the cells which have already undergone a cell culturing process and is undergoing cell culturing in the homothermal module, the entire homothermal module can be detached from the processing system for cell cultures while maintaining the cell culturing state, and another homothermal module can be connected even if a cell culturing process of the cells derived from another human is carried out at the same time. The module that requires a step that takes a long period of time can be once separated from the processing system for cell cultures until the step is completed, and a module of the same type can be separately connected, thereby minimizing the waiting time of the whole system.

Figure 2:
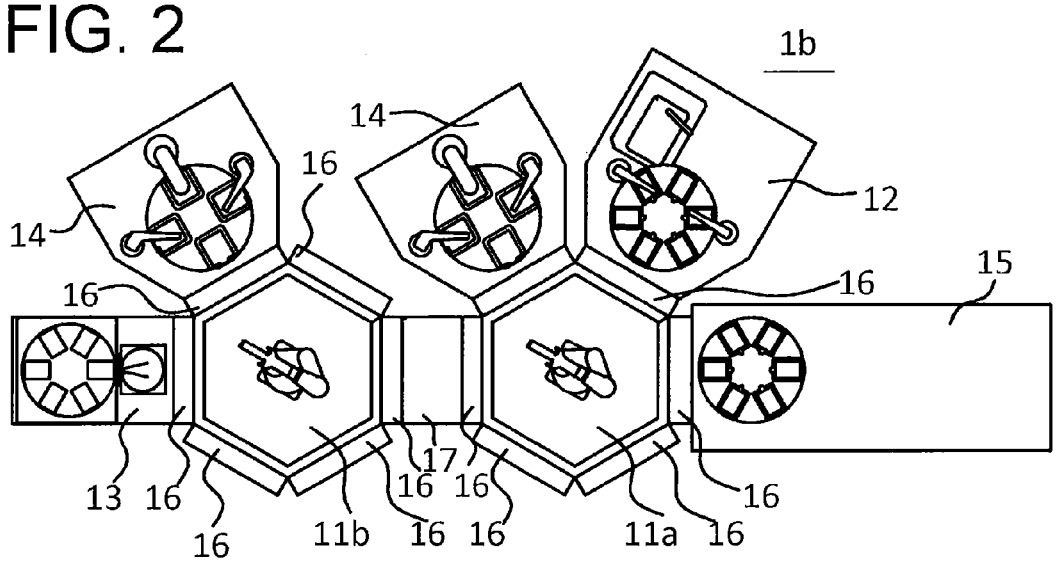
FIG. 2 is a plan view showing a processing system for cell cultures different from the embodiment of FIG. 1.

A processing system for cell cultures shown in FIG. 2 shows another embodiment of the present invention. This processing system for cell cultures 1b connects various processing modules to the outer periphery of a conveyance module 11a. A passing module 17 is provided in the left side of the conveyance module 11a via the attaching/detaching means 16. In the further left side of the passing module 17, another conveyance module 11b is connected via the attaching/detaching means 16.

According to the processing system for cell cultures 1b as described above, the number of modules is not limited to the number of the attaching/detaching means 16 which can be attached to the single conveyance module 11a, and more modules can be added. Therefore, the layout of the modules can be easily changed along with advance and/or change of culturing processes, and modules can be easily added along with advance, complication of the processes, and/or increase in production volume. Herein, the passing module 17 is, for example, a module having, in a chamber thereof, a mounting base such as a culturing plate and a decontaminating-agent supplying aperture 36 which supplies a gas for decontaminating and sterilizing the interior. The chamber is provided with a door capable of sealing/opening an aperture for passing the culturing plate, etc. Therefore, when the door is closed, outside air can be shut off to cause the interior of the chamber to be a closed space. When the door is open, the culturing plate, etc. can be conveyed without contamination by foreign matters.

Moreover, according to the processing system for cell cultures 1b as described above, a plurality of modules having the same function can be combined. The processing system for cell cultures 1b can carry out efficient production at high throughput since the modules can be independently driven simultaneously and parallelly or the modules can be independently driven (controlled) simultaneously and parallelly.

The processing system for cell cultures 1a and 1b can be formed by combining various modules in accordance with processes such as culturing of cells, tissues, etc. Each of the modules is equipped with commands for operating actuators such as a motor, fan, valve, cylinder, Peltier cooler, and heater. Each of the modules is provided with a module control unit which transmits/receives and records electrical signals such as signals, measurement information and/or operation logs from environmental monitors. The environmental monitors are various sensors such as temperature sensor, optical sensor, gas concentration meter, humidity meter, particle counter, position measuring device, and weight scale e.g. . . . . Each of the modules carries out predetermined various processing functions based on various processing procedures stored in the module control device in advance or based on control instructions from a later-described integrated control device.

The processing system for cell cultures 1a and 1b are provided with integrated control devices which can link the operations among the modules and store/manage information which is, for example, obtained by linking ID information of modules which executed the culturing processes with specimen information of cell tissues, etc. and measurement results (operation logs and logs of environment, etc.) including environment information. When electrical signals are transmitted/received from the module control devices of the modules to the integrated control device in association with the ID information of the modules, the fact that with which module the electrical signals have been transmitted/received can be recognized by the integrated control device by recognizing the ID even when one of the modules is detached from a certain module and another module is connected thereto. Thus, various culturing processes can be supported, labor can be saved, cells and tissues can be efficiently produced, and manufacturing cost can be reduced.

A conventional large system is an integrated system equipped with all functions required for culturing processes. In the conventional system, modules cannot be independently separated, which is different from the system of the present invention. Therefore, in the conventional system, while cells derived from one patient are processed, it is difficult to interpose a process of cells derived from another patient. A reason therefor is that, in the conventional system, while one module has been operated for a long period of time, other modules cannot be used, and the system is occupied for a long time.

On the other hand, in the system of the present invention, modules can be attached/detached in accordance with needs. Therefore, in the system of the present invention, occupation of the system by an operating module can be avoided by detaching such module, which operates for a long period of time, from the system. For example, in the system of the present invention, if a module that requires culturing of a long period of time is present in a series of processing steps, the module can be temporally detached from the system and moved to another location. The module can be continuously subjected to progress of culturing at the other location. If necessary, the module can be connected to the system again after completion of the culturing to continue other processes. As a result, the system can be utilized for other culturing processes during the period in which the module is detached and independently subjected to culturing. Therefore, according to the present system, the present system can be efficiently operated by system operation that takes module occupation time into consideration.

If one or some of the plurality of modules fails, such module(s) can be separated from the system and repaired. As a result, operation can be separately carried out by using the modules which have not failed. Therefore, the influence on the whole system caused by failure can be minimized. The system of the present invention is effective in the case in which processing schedules of respective patients are mutually different and in the field of medicine in which quick responses to failure problems of modules are required.

The processing system for cell cultures of the present invention is provided with a module control device having a function of carrying out management of culturing and processing procedures of cells or tissues and a communication means which transmits the measurement results of culturing environments and/or culturing progress. The module control device can order the modules to execute culturing processes and can organize and save data. According to the present system, production of cells based on GMP (Good Manufacturing Practice: manufacturing/quality standards of formulation) can be carried out.

Figure 3:
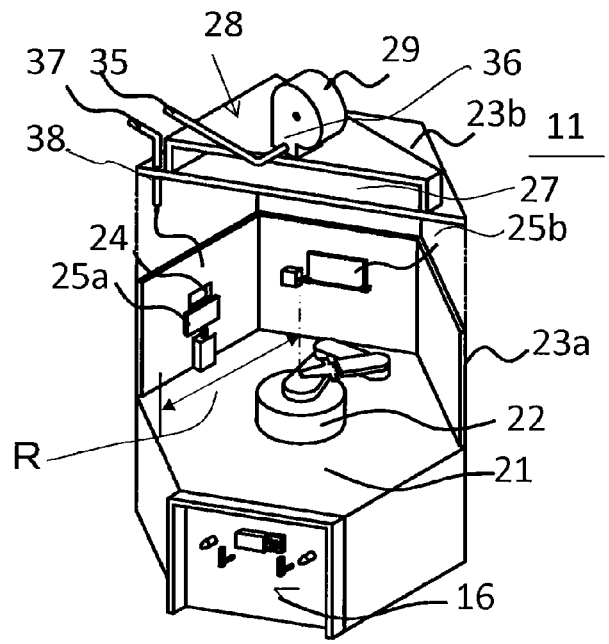
FIG. 3 is a partially-cut-away perspective view of a (conveyance) module 11 of the present invention.

FIG. 3 is a partially-cut-away perspective view of the conveyance module 11, which is a type of the modules of the present invention.

A base which is hexagonal in plan view is denoted by 21, a conveyance robot provided at the center of an upper part of the base 21 is denoted by 22, a chamber (composed of lateral walls 23a of the chamber and a ceiling part 23b of the chamber) which shuts off the scalar-type conveyance robot 22 from the external atmosphere is denoted by 23. An aperture for conveying in/out a conveyance object between the outside of the chamber 23 and the interior of the chamber is denoted by 24. Doors which seal/open the aperture 24 are denoted by 25a and 25b. Furthermore, an attaching/detaching means which attaches/detaches the dispensing module 12, etc. which are the modules attached to the lateral walls of the base and different from the conveyance module 11 is denoted by 16. By virtue of the attaching/detaching means 16, the conveyance module 11 can be coupled or detached while maintaining sealability and sterility. When the modules are coupled and thus a sealed state is obtained while maintaining the sterile state, the cells in the modules can be prevented from being contaminated by germs, other cells. Therefore, in the present system, safety of the quality of cells can be ensured. In the present embodiment, in order to minimize the amount of dust in the modules, a fan filter module (air cleaning module) 28 using, for example, a HEPA filter 27 may be provided.

The decontaminating-agent supplying pipe 35b (decontaminating-agent supplying aperture 36) from the decontaminating-agent supplying module (decontaminating-agent supplying module) 18 can be provided to a fan 29 arranged on the ceiling part 23b of the conveyance module 11, and the decontaminating-agent discharge collecting pipe 37 (decontaminating-agent supplying aperture 38) which discharges/collects the decontaminating/sterilizing gas from the interior of the chamber and sends the gas to the decontaminating-agent supplying module can be connected to the interior of the chamber. The decontamination/sterilization is carried out in order to kill germs and cells attached to the interior of the closed space of the module and the outer surface of the sealed container introduced from the outside of the closed space to the inside thereof. As the decontaminating-agent supplying module, various decontaminating means that supply vapor of hydrogen peroxide and/or ozone, etc. are conceivable. As other decontaminating means, a means that is effective, ensures safety, and can establish validation of decontamination/sterilization can be employed.

The chamber 23 is provided with an internal space having a range slightly larger than an operable range of the scalar-type conveyance robot 22. The range surrounded by the chamber 23 constitutes the first closed space V1 (in the other modules 12 to 15 as well). Herein, the operable range refers to the range of space (occupied space) in which the scalar-type conveyance robot 22 can be operated without interference with peripheral devices, etc. when an arm of the scalar-type conveyance robot 22 is folded as shown in FIG. 3 and subjected to a horizontal turning operation so as to have a minimum turning radius. As this operable range, the shape of the interior space of the chamber is cylindrical in the case of the scalar-type conveyance robot 22 or an arm-slider-type conveyance robot (not shown). In the case of a multi-joint-type conveyance robot, a hemispherical internal space is formed. As a result, the volume of the internal space of the chamber can be minimized.

A gas supplying aperture and a discharging aperture for supplying/discharging the decontaminating gas into/from the chamber are provided in the upper part of the chamber. Therefore, by supplying the minimum hydrogen peroxide gas in order to decontaminate the interior of the chamber, the chamber can obtain a gas atmosphere of a predetermined concentration in a short period of time, a predetermined decontaminated/sterilized state can be maintained, and a decontaminating/sterilizing step can be finished in a short period of time.

A member that undergoes deterioration a little due to the decontaminating agent such as a hydrogen peroxide gas can be used as the material of the interior of the chamber, and joint parts of the member can be appropriately caulked to maintain a predetermined degree of sealing. For example, metal of the interior of the chamber is stainless steel or the like, and silicone rubber or the like can be used as a movable part and a caulking material. When a member that undergoes aging deterioration due to the hydrogen peroxide gas is used, a structure that facilitates replacement is employed. Deterioration due to the gas can be minimized, and the module which can be used over a long period of time can be provided.

The processing system for cell cultures of the present invention is provided with a closed space which is a requisite minimum size. The system is not large the one into which workers enter like a clean room used in the fields of semiconductor and food manufacturing. Therefore, decontaminating/sterilizing time can be shortened, the sterility can be easily maintained, and the system can be manufactured at low cost. Moreover, since the modules can be combined in accordance with needs, the cost of whole system which is a combination of a plurality of modules, can be low. Therefore, the cost of produced cells and tissues can be also reduced.

Figure 4:
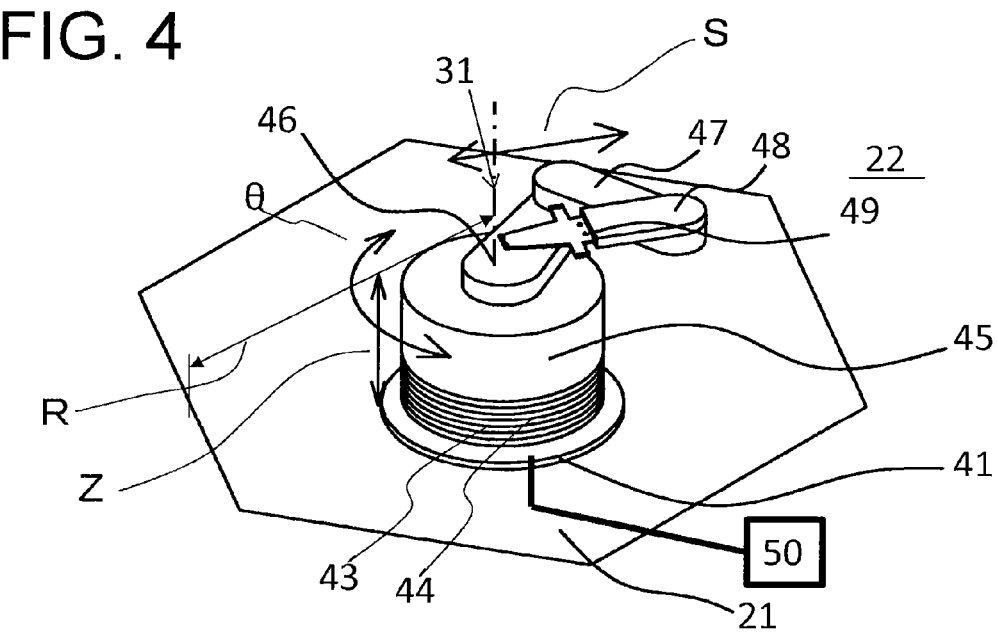
FIG. 4 is a perspective view showing a conveyance robot 22.

The scalar-type conveyance robot 22 shown in FIG. 4 is installed in an inner space covered with the chamber 23 and at the center of an upper part of the base 21. Therefore, the distance from a turning axis 31 (shown by a dashed-dotted line in the drawing) of the scalar-type conveyance robot 22 to the door and the (shortest) distance R therefrom to the inner wall surface of the chamber is constant.

The scalar-type conveyance robot 22 can minimize the internal volume of the chamber 23 when the operable range thereof is minimized. Therefore, when the gas for decontamination is to be supplied, a predetermined decontaminatable/sterilizable concentration can be reached in a short period of time by supplying a minimum amount of the gas.

If the internal volume of the first closed space V1 is large, the gas does not completely fill the interior of the first closed space V1. If the structure of the first closed space V1 is complex, the first closed space is not completely decontaminated. Such problems can be also prevented by reducing the volume thereof and imparting a simple shape thereto.

In the scalar-type conveyance robot 22, a robot base 41 is fixed to the base 21. A raising/lowering means 43 for subjecting the scalar-type conveyance robot 22 to raising/lowering operation is provided on the robot base 41. The raising/lowering means 43 enables linear movement in a Z-direction (not shown) of the drawing by turning a ball screw shaft by actuation of a motor. A turning means 45 is provided on the raising/lowering means 43. The turning means 45 subjects the scalar-type conveyance robot 22 to turning operation (in θ direction) about the vertical direction.

A first arm 46 is rotatably provided on the turning means 45. A second arm 47 is provided at an upper end part of the first arm 46. Furthermore, an end effector 48 on which the culturing plate serving as the conveyance object is to be placed is provided on the second arm 47. The scalar-type conveyance robot 22 can subject the culturing plate, etc. on the end effector 48 to linear movement or curve movement by synchronously moving the first arm 46, the second arm 47, and the end effector 48. Various actuators provided in the scalar-type conveyance robot 22 are actuated based on electric signals from the control device 50 (shown by a bold frame in the drawing). Thus, the scalar-type conveyance robot 22 can convey a micro-plate, a bottle, or a disposable chip of the dispensing module (disposable product supplied to various modules) in the decontaminated/sterilized atmosphere covered with the chamber 23.

An O-ring or a sealing member of a fluorine-based resin or the like which can withstand the decontaminating agent is attached to the revolving part of the scalar-type conveyance robot 22. As a result, the gas for decontamination can be prevented from flowing into the interior of the scalar-type conveyance robot 22 and corroding internal members thereof.

A bellows seal 44 made of resin is attached between a periphery of the robot base 41 of the scalar-type conveyance robot 22 and a periphery of a movable member of the raising/lowering means 43. Therefore, even when the scalar-type conveyance robot 22 undergoes raising/lowering operation, the gas for decontamination/sterilization can be prevented from flowing into the interior of the scalar-type conveyance robot 22 and corroding the interior members thereof.

The end effector has a shape of a flat plate, and the culturing plate, etc. can be placed on the upper part thereof. Conical plate guiding members 49 or, in the case of a nearly cuboidal culturing plate, guiding members which guide four corners or lateral surfaces thereof can be configured to be provided at the upper part of the end effector and in the outer periphery of the culturing plate, etc. placed thereon.

An industrial multi-joint robot, a slider robot, or the like may be used as the conveying means other than the scalar-type conveyance robot.

Figure 5A:
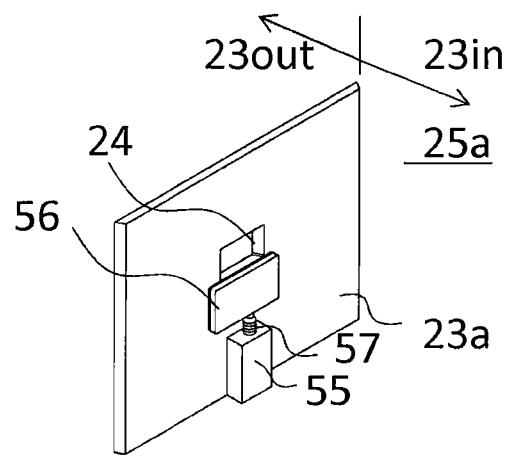
Figure 5B:
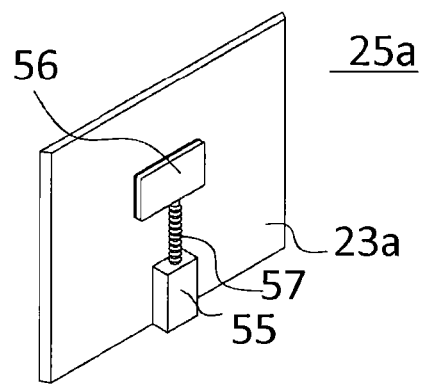

The door 25a shown in FIGS. 5A and 5B is composed of a driving means 55 and a door member 56. In the present embodiment, the driving means 55 is an air cylinder and can open/close the door 56 by upward/downward movement. A bellows seal 57 is attached to a movable part of the driving means 55. By virtue of this, the decontaminating agent is prevented from flowing into the interior of the door driving means and corroding interior members thereof. FIG. 5A shows a state in which the door member 56 is moved down by actuation of the door driving means 55 so that the inside V1 (the side denoted by 23in) of the first closed space V1 and the outside V2 (the side denoted by 23out) are communicated with each other via the aperture 24.

FIG. 5B shows a state in which the door member 56 is similarly moved up to close the aperture 24 and seal the interior of the first closed space V1. A silicone seal 58 is attached to a contact part (in the door side or the chamber side) of the door member 56 and the first closed space V1 (periphery of the aperture 24). The silicone seal has a tubular shape. When a compressed gas is injected into the tube, the tube is swelled and seals the part between the chamber and the door member 56. Other than the present embodiment, sealing by squeezing by the door may be employed.

The door 25b shown in FIG. 3 is a rotary door having a rotation axis parallel to the wall surface 23a of the first closed space V1. A silicone seal is attached to (the door side or chamber side) the contact part of the door member 56 and the first closed space V1 (periphery of the aperture 24). The door can be the rotary driven door which has a motor or a cylinder and a link member attached to the rotation axis. Such a door can seal by evenly squeezing the silicone seal between the door and the wall surface of the interior of the chamber by rotation force. An O-ring of a fluorine-based resin material, a fluorine-based V-seal, or the like is used at the location of rotary drive to prevent the decontaminating gas from flowing into the interior of the rotating means and corroding interior members thereof.

FIGS. 6A-6D show the states in which a module connects with the other module. Reference numeral 23a represents the wall surface 23a of the first closed space V1 of the module above, the right side of the door 56 in the drawings (the region denoted by → S in the drawings) is the interior of the chamber, and the left side (the region denoted by U in the drawing) is outside of the first closed space V1 of the conveyance module 11. The region in the right side of the door member 56a of the other module (the region denoted by → T) is the outside of the first closed space V1. The region V2 (the region of V2 is referred to as a second closed space) is outside of the module and the other module; however, this is a region that serves as interior of the closed space when the apertures 24 and 24a of the module and the other module are communicated with each other.

Figure 6A:
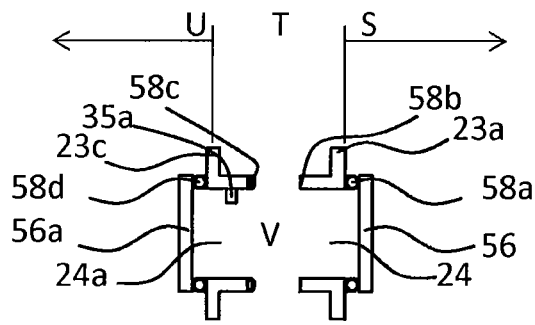
FIGS. 6A-6D show explanatory drawings explaining operation of a case in which two modules are to be connected.
Figure 6B:
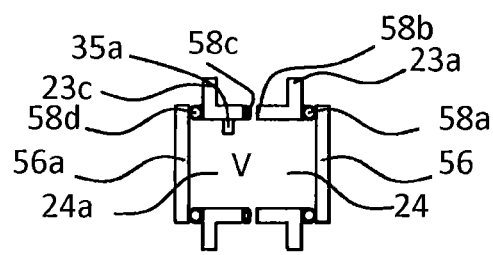
Figure 6C:
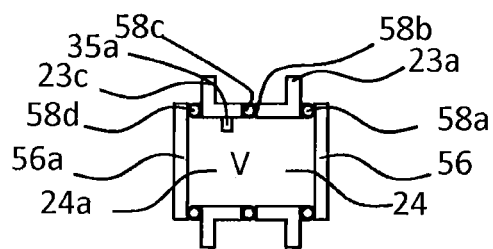

FIG. 6A shows the state before the module (referred to as "first module") and the other module (referred to as "second module") are connected to each other. FIG. 6B shows the state in which the second module (the module in the left side of the drawing) is moved from the state of FIG. 6A to the right side of the drawing up to a position immediately before abutting between a sealing member 58c and a seal receiver 58b. FIG. 6C shows the state in which a gas is injected into the tube to swell it and the seal receiver 58b and the sealing member 58c are abutted each other. By virtue of this, the region V wherein the peripheries of the apertures 24 and 24a are shut off from the outside is in a sealed state (shown in FIG. 6C). At this point, the decontaminating/sterilizing gas is supplied to the region V from the decontaminating/sterilizing gas supplying aperture 35a (in some cases, an unillustrated decontaminating/sterilizing gas discharge collecting aperture provided) to decontaminate/sterilize the interior of the region V.

Figure 6D:
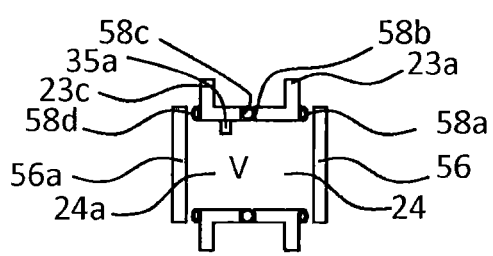

As a result, when the apertures are communicated, the interior of the chamber can be prevented from being contaminated with germs, cells, etc. In FIG. 6D, the gas is discharged from the sealing member 58d, which has been swelled by injecting the gas, so as to form a gap between the door member 56a and the sealing member and separate them from each other. Similarly, the gas is discharged from the sealing member 58a, which has been swelled by injecting the gas, so as to form a gap between the door member 56 and the sealing member and separate them from each other. As a result, the regions V of the first module and the second module can be communicated with each other. When the doors are moved downward, the doors can be opened without wearing the sealing members and the doors (without generating dust by wearing, and without deterioration of the sealing members caused by wearing).

Figure 7A:
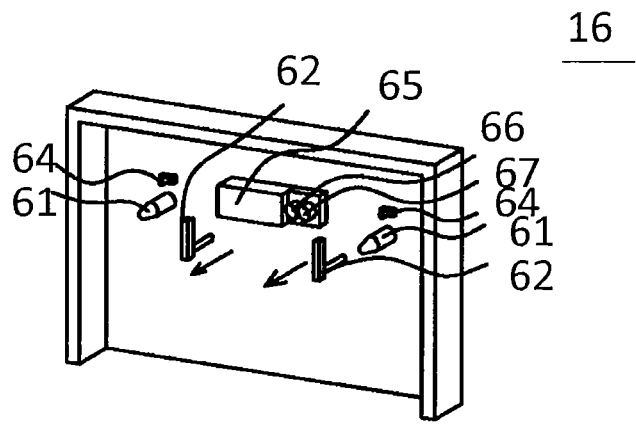
FIGS. 7A-7C show perspective views showing an attaching/detaching means 16.
Figure 7B:
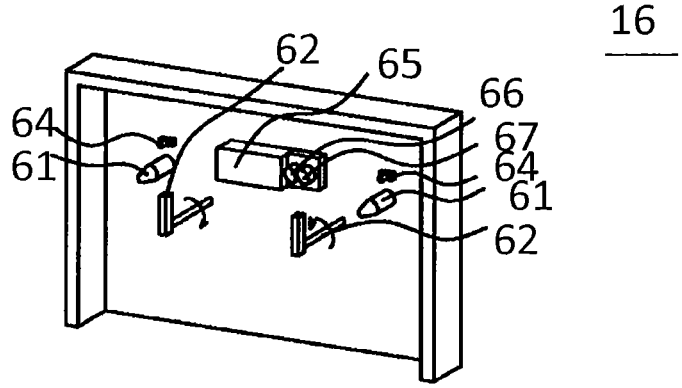
Figure 7C:
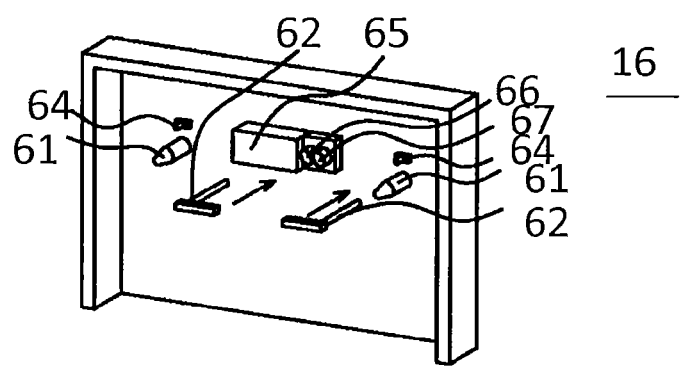

The attaching/detaching means 16 shown in FIGS. 7A-7C is provided with: positioning pins 61, L-shaped key members 62 provided to project in the horizontal direction, a key driving means which subjects the key members 62 to forward/backward movement in a horizontal linear direction and rotary movement, and attachment/detachment detection sensors 64 which detect the fact that the first module and the second module are connected to each other by the actuation of the attaching/detaching means 16 or the fact that they are separated from each other. Reference numeral 65 represents a connector. The connector 65 is, for example, a connector which transmits/receives electric signals between the integrated control device and the module, a connector which supplies electric power to the module, and a connector which supplies a compressed gas, vacuum, other gas (carbon dioxide, nitrogen) and liquid to the module. Reference numeral 66 represents a pipe connector which supplies the decontaminating agent from the decontaminating-agent supplying module via a pipe, and 67 represents a pipe connector which collects the decontaminating/sterilizing gas discharged from the interior of the first closed space V1 of the module. The pipe connector has a decontaminating/sterilizing-gas discharge collection aperture connected to the decontaminating-agent supplying module.

In this embodiment, the attaching/detaching means 16 connects the first module and the second module with each other by: actuating the key driving means 62, subjecting the key members 62 to forward movement in the direction of arrows shown in FIG. 7A, then rotating the key members 62 (in the rotating directions shown in FIG. 7B), and then subjecting the key members 62 to backward movement in the direction of the arrows shown in FIG. 7C. In this process, the positioning pins 61 are fitted into positioning-pin guiding members (members each of which has a recessed part and has a hole part slightly larger than the outer shape of the positioning pin) attached to the second module to be connected at a position corresponding to the positioning pins. As a result, the first module and the second module are connected with each other at predetermined positions. The sensors 64 detect the fact that the module is connected and transmit electric signals indicating the detection to the control device or an integrated management processing module.

By the module connection, the connector 65 of communication lines are also connected. (In the case of connection by wireless LAN, connection is started by receiving electric signals of the sensors 64, for example). When the control device of the second module transmits the ID information of the second module by transmitting an electric signal to the integrated control device, the integrated control device can identify which type of second processing module has been connected to the first module. Furthermore, the pipe connectors 66 and 67 are also connected by this module connection, and thus the decontaminating agent can be supplied to the second module via the first module.

Figure 8A:
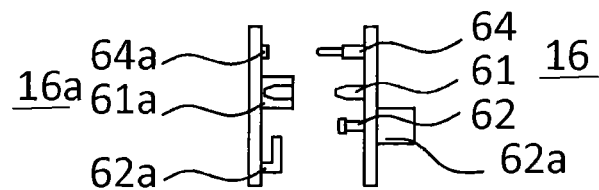
FIGS. 8A-8D shows explanatory drawings for explaining connection operation of the attaching/detaching means 16.
Figure 8B:
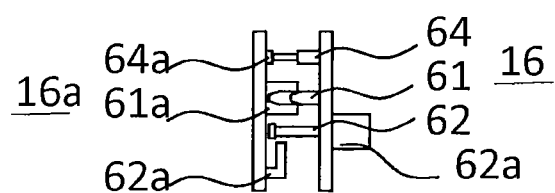
Figure 8C:
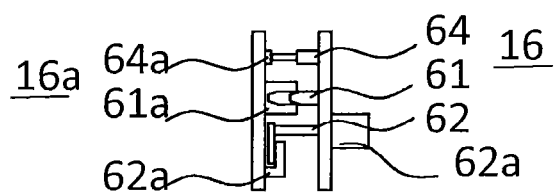
Figure 8D:
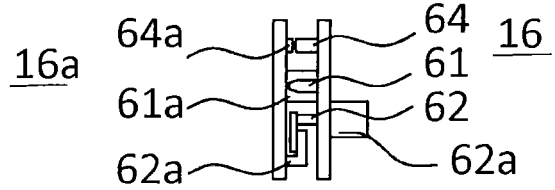

In the present embodiment, the sensors 64 detects the fact that the modules are to be connected, and a pulling operation is started. Thus, attachment/detachment of modules can be supported. The pulling operation will be explained with reference to FIG. 58A-8D. FIG. 8A shows a state in which the attaching/detaching means 16 of the first module and the attaching/detaching means 16a of the second module are separated and not connected with each other. FIG. 8B shows a state in which the second module is moved to the right side of the drawing, wherein the sensor 64 is abutting a sensor receiver 64a. The tip end of the positioning pin 61 is inserted in a recessed part of a positioning-pin receiver 61a.

As a result, the first module and the second module can be smoothly connected with each other without causing misalignment upon attaching/detaching operation. An electric signal for connection operation initiation from the sensor 64 is transmitted to the control device 50. As a result, an operation of moving the key members 62 forward to an attaching/detaching means receiver 16a is carried out (state shown in FIG. 8B). Then, the key members 62 are rotated by actuation of the key driving means 62a of the key members 62 and fitted into key member receivers 62a (state shown in FIG. 8C). Then, when the key members 62 are moved backward by actuation of the key driving means, the attaching/detaching means 16 can pull the attaching/detaching means receiver 16a toward the first module side.

Therefore, a plurality of modules can be combined by increasing/decreasing other modules with respect to one module via the attaching/detaching means. As a result, many types of culturing processes of cells, tissues, etc. are supported.

A plurality of modules having the attaching/detaching means and the same function can be combined with the first module, wherein only one of the modules can be operated or a plurality of the modules can be operated in a simultaneous parallel manner. Therefore, the time required for steps can be managed, and efficient production can be carried out.

The attaching/detaching means 16 is provided between the bases 21 of the plurality of modules, and the function thereof can be exerted regardless of which side the attaching/detaching means 16 is provided to. Another embodiment of the attaching/detaching means 16 may be, for example, an attaching/detaching means on a floor provided with a block member having a recessed part in an upper surface of the member, wherein a connector is attached to the means in the vertical direction so that a pin can be inserted thereto from the upper side to carry out positioning and that the connector is coupled/detached thereto/therefrom by an attaching/detaching operation.

In the present embodiment, the modules 11 to 15 are connected with module control devices 50 and 71a to c via wiring respectively. By virtue of this connection, electric signals, etc. can be received from the module control devices 50 and 71a to c to operate various actuators. Moreover, in that process, the decontaminating-agent supplying module and the modules are connected, and the decontaminating agent is supplied to the modules via pipes. Moreover, in that process, the electric signals from the control devices 50 and 71a to c can be directly or indirectly received to operate the actuators or the decontaminating-agent supplying module. Furthermore, in that process, they are connected with a compression pump module and a vacuum pump module via pipes. Moreover, in that process, the electric signals from the control devices 50 and 71a to c are directly or indirectly received to operate the actuators or the compression pump module and the vacuum pump module. Moreover, in that process, electric power is supplied since they are connected with a power-supply means via wiring.

In this embodiment, the attaching/detaching means 16 may be provided with: the connector 65 of wiring which transmits/receives electric signals, etc. from the control devices 50 and 71a to c, the connector 66 of the pipe which supplies and discharges the decontaminating/sterilizing gas to/from the decontaminating-agent supplying module 18, and a power-supply connector (65); wherein, when the connectors 65 are disposed at the positions corresponding to the connectors 65 of the second module to be connected thereto, the connectors can be configured to be coupled upon connection of the modules so as to transmit/receive the electric signals, etc. to/from the control devices 50 and 71a to c.

The above described second module can be configured to be provided with: a vacuum pump, a compressor, a battery, an electric-signal receiver using wireless LAN, and a control device of the module, separately from the first module. Power may be supplied to the control devices 50 and 71a to c of the modules when coupled with the first closed space V1 of the first module; alternatively, the modules may be configured to be actuated (become a usable state) when a signal of communication initiation is transmitted/received to/from the integrated control device 70.

Examples of the modules include: conveyance modules; carry-out/in modules; isolation primary culturing modules; sub-culturing modules; tube connecting robots; automatic storing modules; conveyance lane modules; cell seeding modules; medium dispensing modules; cell-sheet stacking modules; homothermal modules; other culturing/dispensing/conveyance/measurement/analysis (observation) modules; stocking modules for products (such as micro-plates, tube racks, disposable chips, bottles, reagent tubes, other accessories); measurement modules; carry-out/in modules for plates, etc; and decontaminating/sterilizing-gas supplying modules.

Furthermore, other than the above described modules, various modules can be used depending on the types of cells as culturing targets. Examples of the modules include: a three-dimensional organization module which forms three-dimensional new tissues by using a three-dimensional scaffold, various bio-reactors, a module which imparts stress/strain such as pressure, strain, compression, etc., and a packaging module which packages the processing cells for transportation.

The conveyance module 11 can be provided with: a base; a robot which conveys a culturing plate, etc. to be provided on the base; a chamber which shuts off a movable space of the robot from outside air (covers a lateral part and a ceiling part of the module to fill the interior thereof with the decontaminating/sterilizing gas and prevent the gas from leaking to the outside); a door which opens/closes an aperture through which the culturing plate, etc. are passed to/from inside/outside the chamber; a decontaminating-agent supplying module which supplies the decontaminating agent to the interior of the first closed space V1; and the attaching/detaching means. As another configuration, a moving means can be provided below the module.

The module may also be provided with: a base; a chamber being provided on the base and covering a lateral part and a ceiling part of the module so as to form the first closed space V1 which causes the decontaminating/sterilizing gas to fill the interior thereof and prevents the gas from leaking to the outside; an aperture for passing the culturing plate, etc. to/from the inside/outside the first closed space V1; a door which can open/close the aperture; and a moving means such as skids or a car below the base.

Details of various modules other than the conveyance module will be described below.

<Carry-Out/In Module>

The carry-out/in module is provided with a door for carrying in equipment; and cells and/or culturing solutions required for culturing, medical agents and equipment such as culturing dishes and/or centrifugal tubes are introduced into the carry-out/in module.

The carry-out/in module is provided with operation gloves made from elastomer for moving, unsealing, opening, etc. of the equipment by a worker from outside of the carry-out/in module so that the equipment brought into the module can be manually moved/installed to the vicinity of a culturing processing module by using the operation gloves. Instead of the worker, a belt conveyor or a robot may be used to move it.

<Isolation Primary Culturing Module>

An isolation primary culturing module is provided with a fragmentation module for fragmenting tissue pieces. In addition to the tissue pieces, a centrifugal tube, a petri dish, a culturing solution, etc. are introduced. The means of fragmentation is not limited; however, a method that minimizes the damage applied to the cells is employed. A cell separating module for taking out cells is also provided. The cell separating module decomposes extracellular tissues of the fragmentated tissue pieces with enzymes, rotates them (while decomposing), and isolates cells. Furthermore, objective cells can be taken out by utilizing differences in adhesiveness of the cells, the size and shape of the cells.

The isolation primary culturing module can be configured to be provided with: a mixer serving as a fragmentation module for fragmentating cell pieces and a moving means 8 (for example, dispensing means, single pipetter) which moves the cell pieces from a container (for example, a bottle or a plate) housing them into the mixer.

Moreover, a primary culturing module for further expanding the isolated cells is provided. The primary culturing module is provided with a homothermal module, which can maintain an appropriate gas concentration, and cells are proliferated in a culturing solution under an appropriate environment until the number of cells that enables next sub-culturing is obtained.

The isolation primary culturing module can be configured to be provided with: a take-out means which takes out the fragmentated cell pieces from the mixer; a medium supplying means which supplies a medium to the fragmentated cell pieces; and a homothermal shaking means which carries out shaking operation while maintaining the cells at 37° C.; etc.

In the present embodiment, a fragmentation module of tissues obtained from a living body, a cell separating module, and a primary culturing module collectively form the isolation primary culturing processing module. However, the fragmentation processing module, the cell separation processing module, and the primary culturing processing module may be mutually different modules.

<Sub-Culturing Module>

The sub-culturing module is a module which further increases the number of the cells after the primary culturing to increase them to the number of cells enough for medical treatment.

In the present embodiment, cells are cultured in a closed-type sealed container. This is a large module since the cells are cultured in a large quantity; therefore, this module is not directly coupled to the culturing processing system, and a cell suspension obtained in the closed-type sealed container and the isolation primary culturing processing module is conveyed to a closed-type sealed container in a sub-culturing module through connecting of a tube. The modules may be mutually coupled to carry out transportation by a conveyance robot. In accordance with needs, a plurality of modules, which are mutually the same, may be connecting and culturing.

In a homothermal module provided in the sub-culturing module, proliferation can be carried out by carrying out periodical replacement of a culturing solution under an appropriate environment.

<Dispensing Module>

The dispensing module is a module which uniformly and precisely subjects the suspension of the cells amplified in a large quantity to seeding to a predetermined number of temperature-responsive culturing dishes, removes the medium from the culturing dishes in accordance with needs, and adds a predetermined amount of fresh medium thereto.

The cell suspension conveyed from the sub-culturing module via the tube is stocked in a stacking processing module and subjected to seeding therefrom to a plurality of temperature-responsive culturing dishes or subjected to seeding to a plurality of dishes without being stored via a stocking module. The cells in the seeded suspension are uniformly adhered to the temperature-responsive culturing dishes.

The dispensing module of the present invention is provided with: a rotating table on which a plurality of culturing plates, etc. can be placed; a liquid supplying means which has a dispensing nozzle and supplies liquid; a drainage collecting means which has a drainage collecting nozzle and collects drainage; a nozzle driving means which enables the dispensing nozzle and the drainage nozzle to move in a plane; a nozzle raising/lowering driving means which enables the dispensing nozzle and the drainage collecting nozzle to be moved in a vertical direction separately; a weight measuring means which measures the weight of the culturing plates, etc. from the lower side of the rotating table; and a raising/lowering means of the weight measuring means. The dispensing module is characterized by that, before and after supplying liquid to the culturing plate, the weight measuring means is moved upwards so as to measure the weight of the culturing plate, etc.

This dispensing module can continuously dispense to a plurality of plates accuracy. The speed of the dispensing operation can be increased by providing the dispensing nozzle and the drainage nozzle. Management of the accuracy of dispensing and suction is facilitated by measuring the weight of the culturing plate before supply or suction of a medium and measuring the weight of the culturing plate after the supply or suction. Furthermore, storing the weight data of each plate serves as an effective means that shows validity of the culture supply or culture suction operation.

<Cell-Sheet Stacking Module>

The cell-sheet stacking module is a module which stacks a plurality of cell sheets in the form of sheet to create a new tissue for transplantation having an extremely high cell density.

The thin sheet-shaped cells cultured on the temperature-responsive culturing dish are detached from the dish when the temperature is changed (reduced). Therefore, the temperature of the culturing dish is reduced by a cooler (Peltier cooler) or the like to make the cell sheet, and a plurality of these sheets are stacked with each other by a robot or an actuator. The stacked cell sheets are integrated and become a new tissue having an extremely high cell density. In this manner, the cell-sheet stacking module takes the role of the step of creating a new tissue which can be transplanted by stacking of a plurality of cell sheets through seeding of cells, forming the cells into sheets, and peel-off of the cell sheets.

The cell-sheet stacking module is provided with: a chamber which seals the interior of the module and forms the first closed space V1, and an (opening/closing) door which seals the interior of the device at the aperture of the first closed space V1 through which the culturing plate, etc. are carried out/in. The cell-sheet stacking module is provided with: in the first closed space V1, a rotating table on which a plurality of culturing plates, etc. can be placed; a base member which can carry out raising/lowering operation; an arm which is provided on the base member and can be swung within a vertical plane; a retaining member which retains a cell sheet via gelatin; and a pressing-force measuring means which measures the pressure of pressing the cell sheet between the retaining part and the culturing plate by the raising/lowering operation of the base member. The retaining member is disposed in one side and the pressing-force measuring means is disposed in the opposite side of the retaining member across a central axis of swinging of the arm.

Thus, the cell-sheet stacking module is characterized by having: the rotating table on which the plurality of culturing plates, etc. can be placed; the base member which can carry out raising/lowering operation; the arm provided on the base member so as to be swingable in the vertical plane; the retaining member which retains the cell sheet in one side via gelatin; and, in the other side opposite to the former side across the central axis of swinging, the pressing-force measuring means which measures the pressure of pressing the cell sheet between the retaining part and the culturing plate by the raising/lowering operation of the base member.

The cell-sheet stacking device can continuously stack a plurality of cell-sheets. The stacking can be carried out with constant pressing force by placing the culturing plate containing a cell sheet on the rotating table and sequentially measuring the pressing force of pressing the cell sheet between the retaining member and the culturing plate quickly by the retaining part of the cell stacking device. According to this device, uniform cell-sheet stacking operation is facilitated. Furthermore, when the pressing data of each of the cell sheets is stored, this becomes an effective means that shows validity of the stacking operation.

<Homothermal Module>

The homothermal module (incubator) is for proliferating cells or appropriately maintaining the gas concentration, temperature, and humidity for saving a new tissue until the tissue is transplanted.

<Tube-Connecting Module>

The tube-connecting robot moves the cell suspension, etc. in the closed space to the closed space of another processing module. A tube between one processing module and another module can be connected or detached by this tube-connecting module. According to this module, sterility and sealability are maintained even upon connecting or detachment of a socket (connecting part or connecting connector). This module can be used when a suspension is to be transported by a tube between processing modules.

<Automatic Storing Module>

The automatic storing module stores culturing liquid (media), growth factors, medical agents, cells, containers, etc. required for cells and tissues to be cultured, automatically delivers them in accordance with the cells, and supplies them to processing modules from equipment carry-in door parts of the carry-out/in module and the processing modules.

<Conveyance Lane Module>

The conveyance lane module is a guide for guiding to predetermined locations for coupling the closed spaces of the modules and/or the tubes of the tube-connecting module. A metal tape, rail, guide post, etc. are used as this guide. A module like this can be used when the tube is to be automatically connected.

<Other Modules>

As other modules, the processing module which forms three-dimensional tissues by using the three-dimensional scaffold, the module which applies various bio-reactors and/or a stress-strain such as pressure, tension, and compression, and the packaging module which carries out packaging for transportation are added in some cases.

Figure 9:
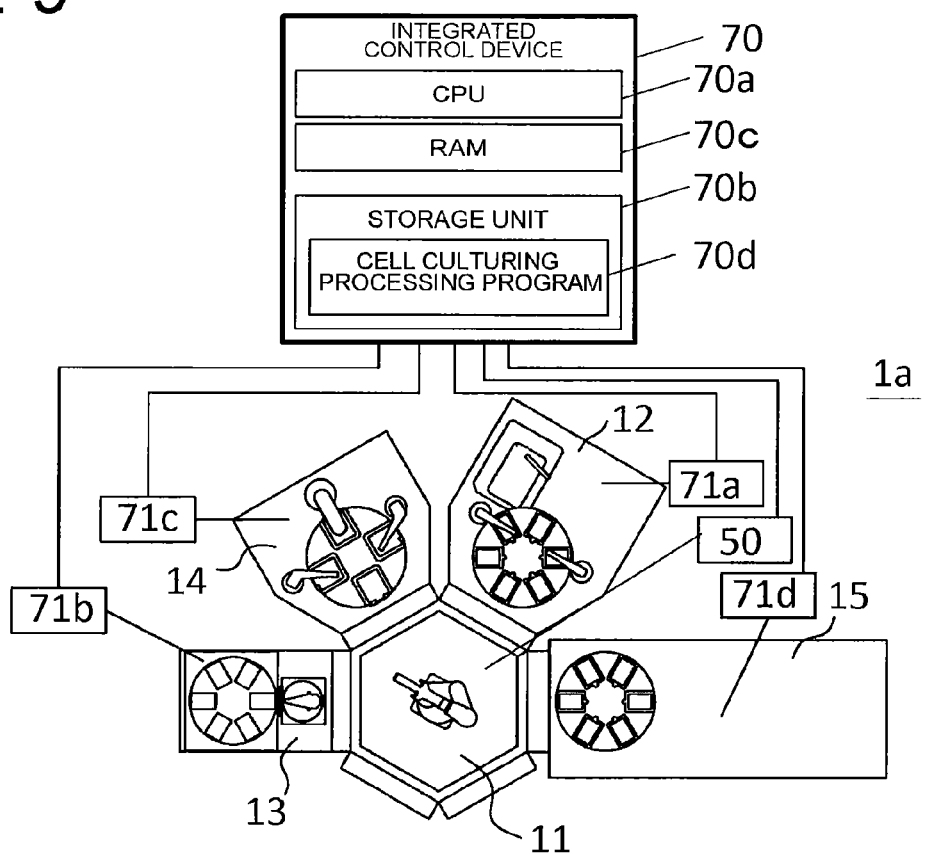
FIG. 9 is a control block diagram of the processing system for cell cultures.

FIG. 9 is a control block diagram of the processing system for cell cultures.

The integrated control device of the present invention will be explained below with reference to FIG. 9.

<Integrated Control Device>

The module of the present embodiment is provided with the control device which transmits/receives electric signals to/from other modules. The control device can transmit/receive electric signals to/from the integrated control device.

The integrated control device links the operations of the modules (causes individual processing modules to transmit/receive electric instructions to operate in accordance with a program) or records the progress of culturing and changes in environmental state and manages a database (collects information from the control devices of the processing modules and manages the information). Furthermore, the integrated control device outputs electric signals of the data to an external printer, computer, or a storage device in accordance with a request of a user.

The integrated control device is provided with a communication means for sharing data with the processing modules and sending/receiving signals thereto/from. The communication means which may be RS23C iEEE, wired, or wireless is only required to solve problems in terms of security. Furthermore, an input module for inputting condition setting of culturing and IDs, etc. of cells or patients and carrying out instructions for operation initiation, viewing of culturing state and database, etc. is provided. Furthermore, a display module which displays the condition setting of culturing, the IDs of cells or patients, culturing state or the like is provided.

The integrated control device may be separated into, for example, a RAM 70c and a CPU 70a as the control device, and a storage unit 70b which is a database management module. The storage unit 70b, for example, records the progress of culturing and changes in the environmental state and manages a database.

Operation control of the processing system for cell cultures 1 (1a, 1b) is carried out by communicating with modules to recognize unique numbers (IDs) of the modules when the plurality of modules are connected and executing a predetermined program stored in the storage unit 70b. The integrated control device 70 also carries out determination whether operation can be carried out or not by the combination of the modules.

The CPU 70a reads the processing program, etc. stored in the storage unit 203, deploys the program to the RAM 70c, and executes the program, thereby carrying out control of the whole processing system for cell cultures 1.

The RAM 70c deploys a processing program, etc. executed by the CPU 70a to a program storing region in the RAM 70c and stores input data and processing results, etc. generated upon execution of the above described processing program in the data storing region.

The storage unit 70b, for example, has a recording medium (illustration omitted) in which programs, data, etc. are stored in advance, and the recording medium is composed of a semiconductor memory, etc. The storage unit 70b stores various data for realizing a function by which the CPU 70a controls the whole processing system for cell cultures 1 (1a, 1b), various processing programs such as a cell culturing processing program 70d, and data processed by execution of these programs, etc.

The cell culturing processing program 70d is a program for causing the CPU 70a to realize a function, etc. of carrying out culturing processing of the cells serving as processing targets based on operation instructions to the combined modules, environmental information of the modules, and information of presence of decontaminating operation.

Each of the modules can be used also independently without being connected to the cell culturing system. Therefore, each of the modules is sometimes provided with: an electric storage (battery) device, a control device, various actuators (heater, motor, and cylinder), an input module, a display module, a compressor, a decontaminating-agent supplying module, etc.

The processing system for cell cultures 1a shown in FIG. 9 is provided with the integrated control device 70. Reference numeral 50 of FIG. 9 denotes the control device of the conveyance module 11, reference numeral 71a denotes the control device of the dispensing module 12, reference numeral 71b denotes the control device of the homothermal module 13, reference numeral 71c denotes the control device of the cell-sheet stacking module 14, and reference numeral 71d denotes the control device of the carry-out/in module 15 for the culturing plates, etc.

The integrated control device 70 is provided with: an input module for inputting the setting of culturing condition, information of the cells to be cultured, etc. and ordering initiation of a culturing process; a display module which displays the culturing conditions, information of cells, operation state, etc.; a communication means which receives information from the modules, transmits ordering signals, and sends the data, which has been transmitted from the modules, to the storage unit; and a control device which controls the modules.

Each of the modules can be operated independently. Also, the modules can automatically operate cell culturing processes in cooperation by carrying out communication between the modules by the integrated control device 70. Communication is carried out between the modules and the integrated control device 70 by LAN cables, wireless LAN, or other communication means. Progress information of the operated steps, culturing environment data, and data of, for example, pass/fail determination of culturing steps are transmitted from the modules to the integrated control device 70. The integrated control device orders the modules to initiate the decontaminating/sterilizing processes or cell culturing processes.

The storage unit 70b is electrically connected to: an input module for inputting orders of retrieval, saved destination of data; a database management module which organizes transmitted data and forms the data into a database; a display module which displays ordered contents and results; and an output module which outputs data to another storage device or a printer, etc.

When a program which isolates cells is executed in the processing system for cell cultures of the present invention, the tissues obtained from a living body is introduced into the closed space, fragmentated, and decomposed by enzymes, and cells thereof are separated and isolated. The cells after isolation is subjected to primary culturing, amplification culturing, and organization, thereby forming a cell suspension or new tissue which can be transplanted while maintaining the sterile state. The cell suspension or the new tissue is tested, packaged, shipped, and cultured. Various data (information by environmental monitoring, etc.) in these steps is transmitted to the storage unit 70b of the integrated control device 70 or another storage device and stored (saved) therein.

An example showing role sharing among the control devices 71a to 71d of the modules and the integrated control device 70 in the steps of the cell culturing system of the present invention is shown. The role sharing from A1 to A16 is as described below.

A1. An operator inputs an ID and a password by the input module. An electric signal from the input module is received by the integrated control device. The integrated control device distinguishes the operation contents which can be carried out by the authority of the operator. Furthermore, the authorized operator inputs necessary items such as patient ID, culturing conditions from the input module.

As a result, the operator can select a program of an appropriate operation procedure from among programs of various operation procedures incorporated in the integrated control device.

A2. The modules to be used in the operation send signals indicating that operation preparation has been completed to the integrated control device.

A3. The integrated control device confirms operation-preparation completion signals from the modules about the operation.

A4. When confirmed, the integrated control device outputs commands for mutually connecting the first closed spaces V1 of the modules to the modules.

A5. The control devices of the connected modules check by the sensor, etc. whether the connection has been reliably carried out.

A6. When completion of reliable connection is confirmed, the control devices of the modules send signals to the integrated control device.

A7. The integrated control device outputs an order to initiate a decontaminating step to the decontaminating-agent supplying module.

A8. Decontamination of the first closed space V1 and the second closed space V2 is executed by the decontaminating-agent supplying module.

A9. When the decontamination is completed, a decontamination completion signal is sent from the decontaminating-agent supplying module to the integrated control device. The decontamination state of the modules (whether decontaminated or not decontaminated) is stored in the integrated control device together with the module IDs.

A10. The integrated control device which has received the signal of decontamination/sterilization completion gives a command of operation by a program to the module which is to be operated first.

A11. The module which has received the operation order is operated by the ordered program.

A12. The module which is being operated periodically sends data of predetermined items such as time of operation, environmental data, and confirmation results of check points to the integrated control device. The data above may be saved also in the modules.

A13. The integrated control device saves the transmitted data in the database.

A14. If occurrence of failure or abnormality is detected during operation of the module, the data thereof is transmitted to the integrated control device. Depending on the contents thereof, recovery operation is automatically carried out in the module. If recovered, the data (contents, time, etc.) thereof is transmitted to the integrated control device.

A15. The integrated control device saves the abnormality data and recovery data in the database.

A16. If the program in the module is finished, a termination signal is transmitted to the integrated control device.

A17. If the module has to be separated, the integrated control device transmits a separation command; and, if the module has to be coupled, the integrated control device transmits a connection command. If the module is to be coupled in the middle of the process, the coupling is carried out after confirming the decontamination/sterilization state thereof from the module ID of the module which is to be newly coupled.

A18. Thereafter, operation of each of the following modules is repeated from A2 to A17.

A19. When all of them are finished, various data transmitted from each of the modules is saved as a series of data of each specimen and, in accordance with needs, is output to another storage device, a printer, or the like.

Figure 10A:
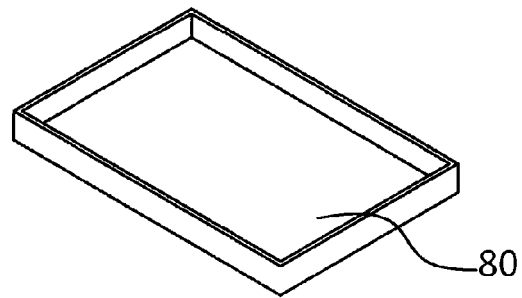
FIGS. 10A and 10B is a perspective view showing a culturing plate, etc.
Figure 10B:
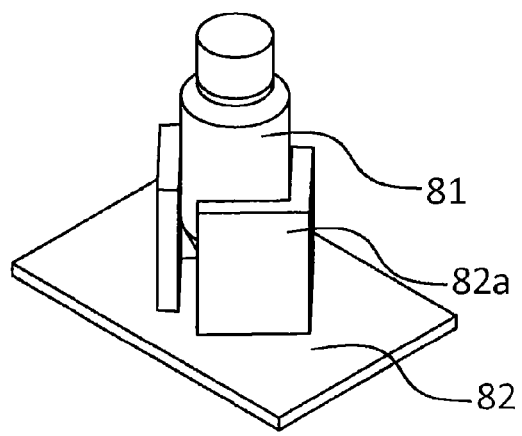

The culturing plate, etc. in the present invention are, for example, a culturing plate shown in FIG. 10A and a reagent bottle 81, a reagent bottle bracket 82, and a plate for sheet-cell retaining member of the cell-sheet stacking module shown in FIG. 10B. In the reagent bottle bracket 82 for conveying the reagent bottle 81, a guide member 82a is attached on the reagent bottle bracket 82 so that the reagent bottle 81 can be conveyed in an upright state.

Figure 11:
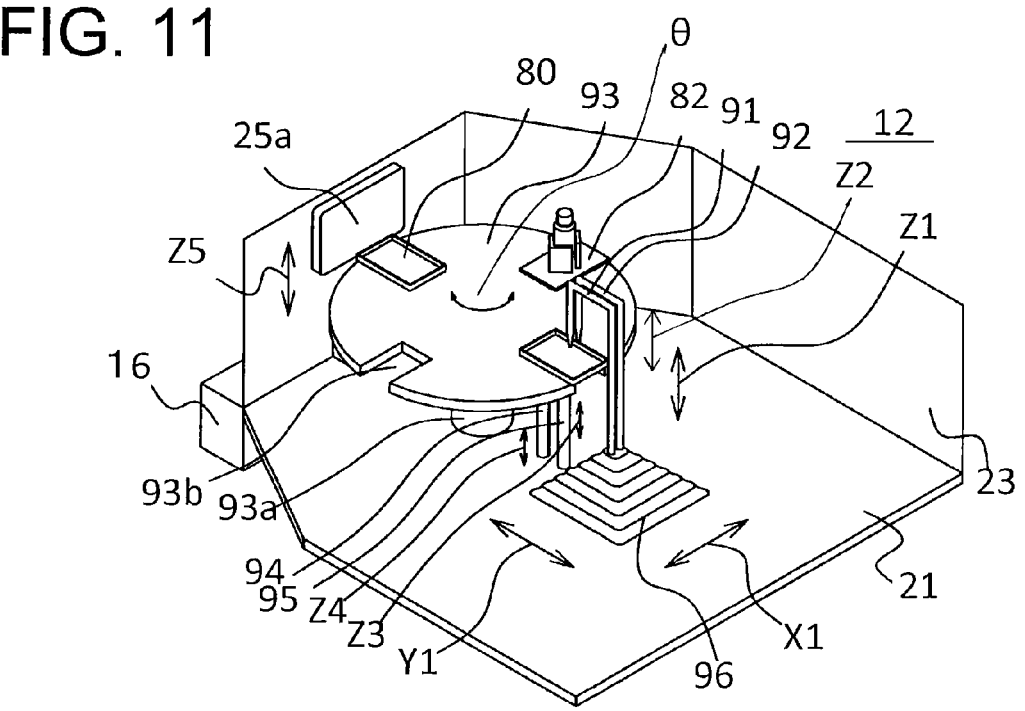
FIG. 11 is a partially-cut-away perspective view of a (dispensing) module which is different from FIG. 3.

The module (dispensing module) 12 shown in FIG. 11 is characterized by being provided with: a rotating table 93 on which the plurality of culturing plates, etc. 80 can be placed; a liquid supplying means which has a dispensing nozzle 91 and supplies liquid; a drainage collecting means which has a drainage collecting nozzle 92 and collects drainage; a nozzle driving means which can move the dispensing nozzle 91 and the drainage collecting nozzle 92 in a plane; a nozzle raising/lowering drive means (not shown) which enables the dispensing nozzle 91 and the drainage collecting nozzle 92 to be moved in a vertical direction separately; a weight measuring means 97 which lifts up the culturing plate, etc. 80 from the lower side of the rotating table 93 and measures the weight thereof; and a raising/lowering means 95 of the weight measuring means; wherein, before and after the liquid is supplied, the weight measuring means is moved upward via an aperture 24 (no shown) of the rotating table to measure the weight of the culturing plate 80, etc.

In the rotating table 93, an opening 93b is arranged below the location where the culturing plate 80 is placed so that the culturing plate 80, etc. can be placed by the conveyance robot 22 (not shown). The plurality of culturing plates 80 can be placed on the rotating table 93. A cover opening/closing means, etc. which opens/closes a cover of the culturing plates 80 are disposed in the periphery of the rotating table 93. When the culturing plates 80 on the rotating table 93 are sequentially subjected to divided operations by rotating the rotating table 93 at a predetermined rotation angle, efficient steps can be carried out. The conveyance robot 22 can lift up the culturing plate 80 from the rotating table by inserting the end effector 48 to the lower side of the culturing plate 80 and carrying out moving the plate up. As a result, the conveyance robot 22 can smoothly convey the culturing plate 80 without dropping or tilting the plate during conveyance. By actuation of the rotating table, the culturing plate 80 can be moved by rotation (in the direction of e in the drawing) to the vicinity of the dispensing nozzle 91 (drainage collecting nozzle 92). The dispensing nozzle 91 can be moved in the directions of Z1, X1, and Y1 in the drawing, and the drainage collecting nozzle 92 can be moved in the directions of Z2, X1, and Y1. Driving means thereof are provided below the base 21 and sealed by a bellows seal 96. Therefore, the risk of corrosion or deterioration of the driving means by the decontaminating/sterilizing gas can be reduced.

Figure 12A:
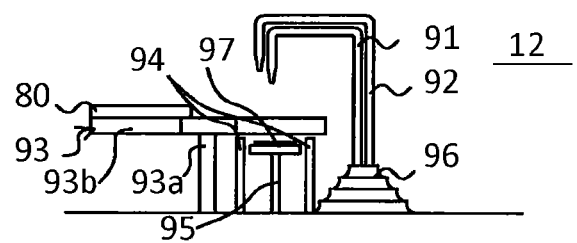
FIGS. 12A-12D show explanatory drawings showing dispensing operation of the (dispensing) module 12.
Figure 12B:
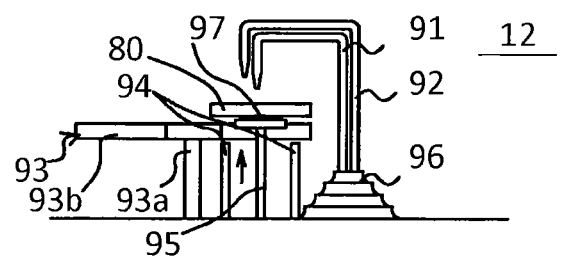
Figure 12C:
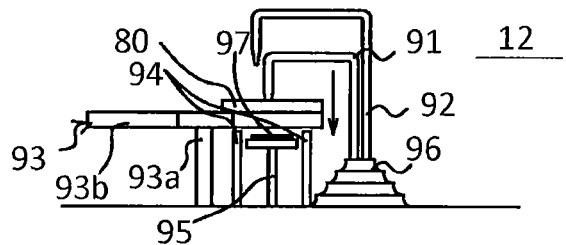
Figure 12D:
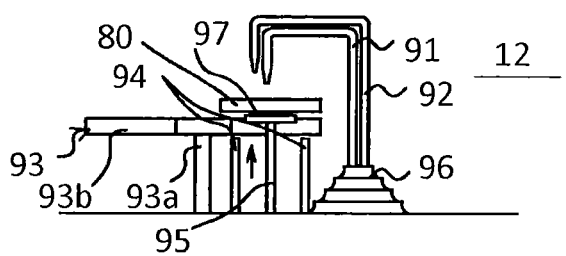

FIG. 12A shows a state in which the culturing plate 80 is placed on the rotating table 93. FIG. 12B shows a state in which a rotating shaft 93a of the rotating table 93 is moved by rotation of 180 degrees from the state of FIG. 12A, and the weight measuring means 95 below the rotating table 93 is moved up so as to place the culturing plate 80 on a measurement table 97 (weight measurement is carried out). FIG. 12C shows a state in which the weight measuring means 95 is lowered from the state of FIG. 12B, and the dispensing nozzle 91 is lowered. FIG. 12D shows a state in which, after dispensing operation, the dispensing nozzle 91 is moved up and then the weight measuring means 95 is moved up to carry out weight measurement. Then, an operation command and weight measurement are carried out by the control device 71a, and operation logs and/or weight measurement data are transmitted to and received by the integrated control device together with the module ID.

Figure 13A:
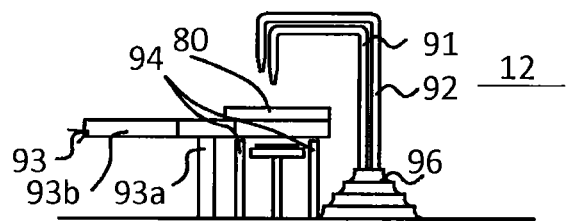
FIGS. 13A-13C show explanatory drawings showing drainage collecting operation of the (dispensing) module 12.
Figure 13B:
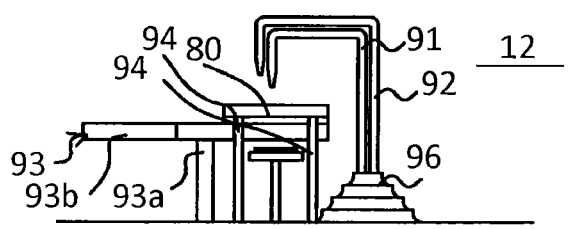
Figure 13C:
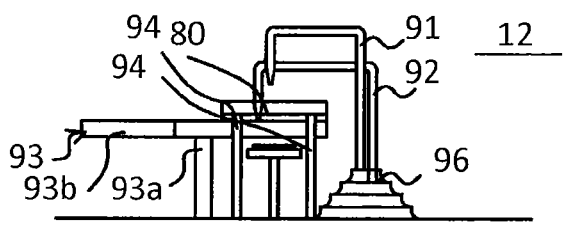

FIGS. 13A-13C show explanatory drawings showing the drainage collecting operation of the module (dispensing module) 12. FIG. 13A shows a state in which the culturing plate 80 which requires replacement of a medium solution is placed on the rotating table 93. FIG. 13B shows a state in which a plate tilting means 94 is moved up so as to lift up a one-side bottom part of the plate of the culturing plate 80 and tilt the plate. FIG. 13C shows a state in which the drainage collecting nozzle 92 is lowered to collect drainage. Then, an operation command is carried out by the control device 71a, and operation logs and/or various data are transmitted and received by the integrated control device together with the module ID.

Figure 14:
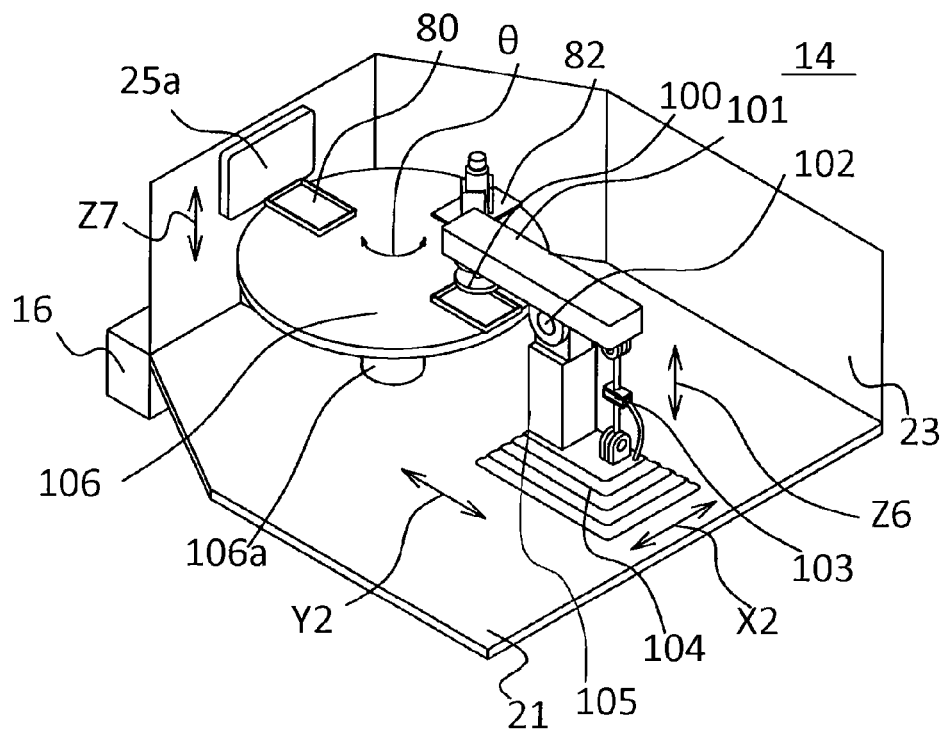
FIG. 14 is a perspective view showing a module (cell-sheet stacking module) 14 different from FIG. 11.

FIG. 14 is a perspective view showing the cell-sheet stacking module 14, wherein reference numeral 100 denotes the retaining member which retains the cell sheet. The retaining member 100 is attachably/detachably provided at a tip-end lower part of an arm 101. The retaining member 100 has a part to be in contact with the cell sheet and a gel-like matter is applied to the part. The gel-like matter is, for example, gelatin. Therefore, the cell sheet can be pasted thereon and lifted up. The arm 100 is attached to an upper part of a (quadrangular prism shaped) base member swingably in a vertical plane. The retaining member 100 is provided in the left side of the drawing, and a pressing-force measuring means 103 which measures pressing force (weight) is provided in the right side of the drawing, with a swinging rotation shaft 102 of the arm interposed therebetween. A lower part of a base member 105 is sealed by a bellows seal 104. Below the base member, a driving means (not shown) which can move the base member 105 in the X2 direction and the Y2 direction in a horizontal plane and a raising/lowering driving means which subjects the base member to raising/lowering operation are provided.

In order to measure pressing force by the pressing-force measuring means 103, when the base member 105 is lowered by actuation of the raising/lowering means to press the retaining part against the cell sheet in the culturing plate 80, measurement can be carried out. In that process, the retaining member 100 (point of effort) attached to the tip end of the arm 101 is swung about a swinging rotation shaft (point of support, fulcrum) and pushes the pressing measuring means 103 (point of action). The pressing-force measuring means 103 is, for example, a load cell.

The result information measured by the pressing-force measuring means 103 is transmitted or received as an electric signal via the control device 71c (not shown) of the cell-sheet stacking module 14 or directly to the integrated control device 70. Based on the measurement result, the cell-sheet stacking module 14 carries out operation control (feedback control, etc.) so that the pressing force becomes constant; as a result, a uniform cell layer can be formed.

Reference numeral 106 denotes a rotating table on which the plurality of culturing plates 80, etc. can be placed. The rotating table 106 is provided with a rotating shaft 106a. The rotating shaft 106a is sealed by an O-ring or the like and can be subjected to rotary drive by actuation of a rotary driving means below the base 21.

Therefore, when a plurality of cell sheets are to be continuously stacked, an efficient stacking step can be realized by placing the plurality of culturing plates 80, which house cell sheets, arranged on the rotating table and sequentially carrying out stacking operations.

This system can be installed in existing limited space such as a location like a hospital and used therein, and cells and tissues according to GMP (Good Manufacturing Practice: manufacturing/quality standards of formulation) can be prepared also in use at such a location. Moreover, a plurality of systems are installed to contribute to cell and tissue culturing businesses in which tissues brought in from hospitals are accepted and cultured.

REFERENCE NUMERALS

1: Processing system for cell cultures
11: Conveyance module
12: Dispensing module
13: Homothermal module
14: Cell-sheet stacking module
15: Carry-out/in module of culturing plate, etc.
16: Attaching/detaching means

The invention claimed is:

1. A processing system for cell cultures comprising:
   a plurality of modules that can be mutually connected;
   a first closed space provided in each of the modules;
   a door that opens/closes an aperture provided in the first closed space;
   a sealing tube or silicone seal provided at a peripheral part of the aperture for filling a gap between the door and a module; and
   a decontaminating-agent supplying container configured to supply a decontaminating agent, the decontaminating-agent supplying container including one or more supplying pipes that supply the decontaminating agent made into vapor, gas, or mist;
   wherein the decontaminating agent is supplied to the first closed space by the decontaminating-agent supplying container;
   the decontaminating agent is supplied to a second closed space formed by sealing tubes or silicone seals and the doors of one and the other modules connected to each other, to form an integrated closed space maintaining the plurality of connected modules in a sterile state.

2. The processing system for cell cultures according to claim 1, further comprising:
   module control devices that include circuitry, the module control devices are configured to carry out control so that the modules execute predetermined process in accordance with a command from the module control devices, wherein the module control devices are configured to carry out management of culturing and processing procedures of cells or tissues; and
   an integrated control device that includes a CPU, a RAM, and a storage unit, the integrated control device being electrically connected to the circuitry of the module control devices of the modules connected each other via the connecting member and controls operation of the modules; wherein
   the integrated control device carries out communication with the plurality of connected modules, recognizes IDs of the modules, and carries out operation commands corresponding to the IDs with respect to the modules so as to associate the plurality of connected modules and subject a series of processing steps of various culturing processes to an integrated process or separately execute the various cell culturing processes, and
   wherein the module control devices transmit the measurement results of culturing environments and/or culturing progress to the integrated control device.

3. The processing system for cell cultures according to claim 1 or 2,
   further comprising a conveyance module, to which the modules are connected, provide with a conveyance robot inside of the conveyance module, the conveyance module including at least one aperture, at least one door, and/or connecting material; wherein
   the conveyance robot moves a conveyance object from the first closed space of one of the connected modules to the first closed space of the other module via the second closed space.

4. The processing system for cell cultures according to claim 3, wherein
   the sealing tube or silicone seal has a hollow shape and an injector is configured to inject a gas, etc. into the sealing tube or silicone seal; wherein, the sealing tube or silicone seal is swelled to fill the gap between the door and a module and to hermetically seal the second closed space.

5. A module connecting method of the processing system for cell cultures according to claim 4, the method comprising:
   a step of installing the plurality of modules with a gap therebetween;
   a step of swelling sealing tubes or silicone seals provided on the plurality of modules so as to fill the gap and connect the plurality of modules;
   a step of supplying the decontaminating agent to the second closed space formed by the plurality of sealing tubes or silicone seals and the plurality of doors from the decontaminating-agent supplying container to decontaminate interior of the second closed space; and
   a step of opening the doors to communicate the first closed space and the second closed space with each other and form an integrated sterile closed space.

6. A module connecting method of the processing system for cell cultures according to claim 3, the method comprising:
   a step of connecting each of the plurality of modules respectively via a sealing tube or silicone seal;
   a step of supplying the decontaminating agent to the second closed space formed by the plurality of sealing tubes or silicone seals, and the plurality of doors from the decontaminating-agent supplying container to decontaminate interior of the second closed space; and
   a step of opening the doors to communicate the first closed space and the second closed space with each other and form an integrated sterile closed space.

7. The processing system for cell cultures according to claim 1 or 2, wherein
   the sealing tube or silicone seal has a hollow shape and an injector is configured to inject a gas, etc. into the sealing tube or silicone seal; wherein, the sealing tube or silicone seal is swelled to fill the gap between the door and a module and to hermetically seal the second closed space.

8. A module connecting method of the processing system for cell cultures according to claim 7, the method comprising:
   a step of connecting each of the plurality of modules respectively via a sealing sealing tube or silicone seal;
   a step of supplying the decontaminating agent to the second closed space formed by the plurality of sealing tubes or silicone seals, and the plurality of doors from the decontaminating-agent supplying container to decontaminate interior of the second closed space; and
   a step of opening the doors to communicate the first closed space and the second closed space with each other and form an integrated sterile closed space.

9. A module connecting method of the processing system for cell cultures according to claim 7, the method comprising:
   a step of installing the plurality of modules with a gap therebetween;
   a step of swelling sealing tubes or silicone seals provided on the plurality of modules so as to fill the gap and connect the plurality of modules;
   a step of supplying the decontaminating agent to the second closed space formed by the plurality of sealing tubes or silicone seals and the plurality of doors from the decontaminating-agent supplying container to decontaminate interior of the second closed space; and
   a step of opening the doors to communicate the first closed space and the second closed space with each other and form an integrated sterile closed space.

10. A module connecting method of the processing system for cell cultures according to claim 1 or 2, the method comprising:
   a step of connecting each of the plurality of modules respectively via a sealing tube or silicone seal;
   a step of supplying the decontaminating agent to the second closed space formed by the plurality of sealing tubes or silicone seals and the plurality of doors from the decontaminating-agent supplying container to decontaminate interior of the second closed space; and
   a step of opening the doors to communicate the first closed space and the second closed space with each other and form an integrated sterile closed space.

* * * * *